United States Patent [19]

Miura et al.

[11] Patent Number: 5,112,384
[45] Date of Patent: May 12, 1992

[54] 3-(SUBSTITUTED PHENYL) PYRAZOLE DERIVATIVES HERBICIDAL COMPOSITION CONTAINING THE SAME AND METHOD OF CONTROLLING WEEDS USING SAID COMPOSITION

[75] Inventors: Yuzo Miura, Nishinomiya; Masanobu Ohnishi, Osaka; Tsutomu Mabuchi, Kawachinagano; Isao Yanai, Osakasayama, all of Japan

[73] Assignee: Nihon Nohyaku Co., Ltd., Tokyo, Japan

[21] Appl. No.: 659,729

[22] Filed: Feb. 25, 1991

[30] Foreign Application Priority Data

Feb. 28, 1990 [JP] Japan ................................. 2-048071

[51] Int. Cl.$^5$ .................... A01N 43/56; C07D 233/70
[52] U.S. Cl. ......................................... 71/92; 548/376
[58] Field of Search .............................. 548/376; 71/92

[56] References Cited

U.S. PATENT DOCUMENTS 5,032,165 7/1991 Miura et al. ..................... 548/376

Primary Examiner—Robert W. Ramsuer
Attorney, Agent, or Firm—Cushman, Darby & Cushman

[57] ABSTRACT

A 3-(substituted phenyl)pyrazole derivative or a salt thereof, the derivative being represented by the general formula

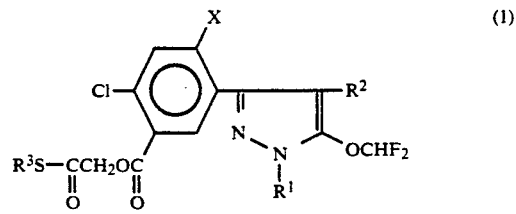

wherein, X denotes halogen, $R^1$ denotes lower alkyl, $R^2$ denotes halogen and $R^3$ denotes lower alkyl, lower alkenyl or benzyl group, a process for producing said pyrazole derivative, a herbicidal composition containing said pyrazole derivative as an active ingredient, and a method of controlling weeds by applying said composition.

8 Claims, No Drawings

3-(SUBSTITUTED PHENYL) PYRAZOLE DERIVATIVES HERBICIDAL COMPOSITION CONTAINING THE SAME AND METHOD OF CONTROLLING WEEDS USING SAID COMPOSITION

The present invention relates to 3-(substituted phenyl)pyrazole derivatives or salts thereof, a process for producing said derivatives or salts, and a to herbicidal composition comprising said derivatives or salts and methods for applying said herbicidal compositions.

The 3-(substituted phenyl)pyrazole derivatives are represented by the general formula

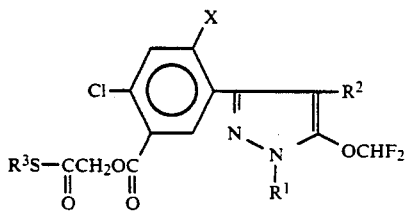

(1)

wherein,

X denotes halogen, $R^1$ denotes lower alkyl, $R^2$ denotes halogen and $R^3$ denotes lower alkyl, lower alkenyl or benzyl group.

The present inventors made intensive studies in order to develop a novel herbicide and as a result have found that 3-(substituted phenyl)pyrazole derivatives represented by general formula (I) (hereinafter, simply referred to as formula (I)) and salts thereof are novel compounds, not yet written in literature, and they show excellent herbicidal effects on weeds even at lower dosages. Based on this finding, the present invention has been accomplished.

Prior to the present invention, compounds considered analogous to the present inventive compounds were disclosed as herbicides in Japanese Patent Application Kokai Nos. Sho. 50-117936, Sho. 52-91861, Sho. 54-70270, and Sho. 55-9062 and in other literature.

However, the present inventive 3-(substituted phenyl)pyrazole derivatives represented by formula (I) or salts thereof have never been disclosed and show superior herbicidal effects at lower dosages than those where the compounds disclosed in the above patent applications do.

The present inventive 3-(substituted phenyl)pyrazole derivatives represented by general formula (I) and salts thereof include structural isomers as shown below.

These structural isomers are produced simultaneously during the production of 3-(substituted phenyl)-pyrazole derivatives and each isomer can be isolated by a suitable separating method, e.g. recrystallization or column chromatography.

The scope of the present invention also includes these structural isomers.

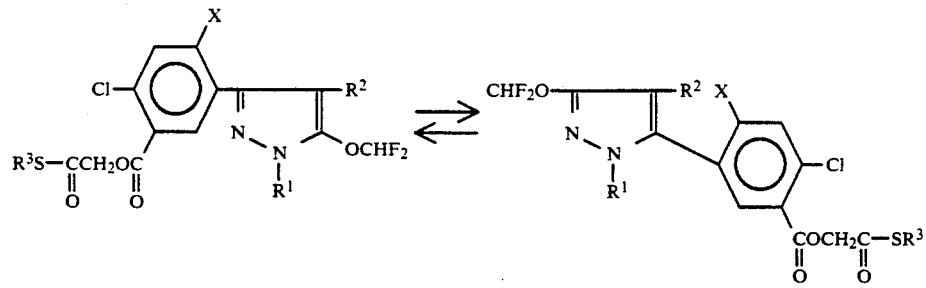

In this formula, X, $R^1$, $R^2$ and $R^3$ are defined above.

The substituent $R^1$ in 3-(substituted phenyl)pyrazole derivatives represented by formula (I) and salts thereof is lower alkyl group which can be examplified by methyl, ethyl, n-propyl, i-propyl, n-butyl, i-butyl, s-butyl, and t-butyl, of which preferred are methyl.

The substituent $R^2$ is a halogen atom which can be examplified by chlorine, bromine, iodine, and fluorine, of which preferred is a chlorine atom.

The substituent $R^3$ can be examplified by lower alkyl having 1–6 carbon atoms, lower alkenyl having 2–6 carbon atom and benzyl groups, of which preferred are lower alkyl groups and particularly preferred are methyl and ethyl groups.

The substituent X is a halogen atom which can be examplified by chlorine, bromine, iodine, and fluorine, of which preferred is a chlorine atom.

Salts of 3-(substituted phenyl)pyrazole derivatives represented by formula (I) are of mineral acids including, e.g. sulfuric acid and hydrochloric acid and of organic acids including, e.g. p-toluenesulfonic acid.

Salts of 3-(substituted phenyl)pyrazole derivatives represented by formula (I) can be produced by treating these derivatives with a suitable mineral acid or organic acid.

Typical processes for producing 3-(substituted phenyl)pyrazole derivatives represented by formula (I) or salts thereof can be illustrated by the following reaction scheme.

Reaction Scheme

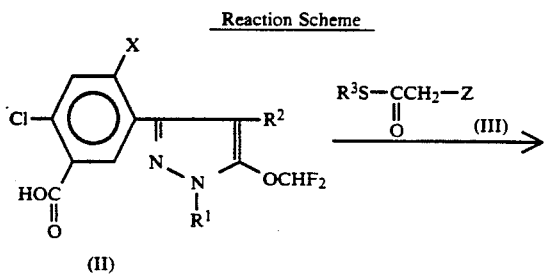

-continued
Reaction Scheme

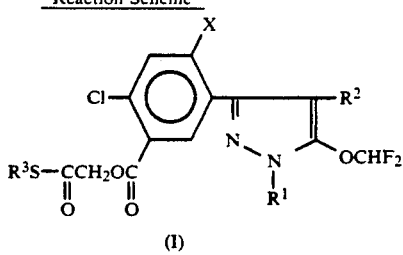

(I)

In this formula, X, $R^1$, $R^2$ and $R^3$ are defined above, and Z denotes halogen atom.

That is, 3-(substituted phenyl)pyrazole derivatives represented by formula (I) can be produced as follow: a pyrazole derivative represented by formula (II) is reacted with a halide represented by formula (III) in an inert solvent in the presence or absence of a base to produce the 3-(substituted phenyl)pyrazole derivatives represented by formula (I).

Any inert solvent may be used in this reaction that does not markedly hinder the reaction from proceeding. Such a solvent includes, though is not limited to; halogenated hydrocarbons, e.g. methylene chloride, chloroform, and carbon tetrachloride; aromatic hydrocarbons, e.g. benzene, toluene, and xylene; aliphatic hydrocarbons, e.g. n-hexane, and cyclohexane; ketones, e.g. acetone, methyl ethyl ketone, and cyclohexanone; ethers, e.g. diethylether, tetrahydrofuran, and dioxane; lower fatty acid amides, e.g. dimethylformamide, and dimethylacetamide; water; dimethylsulfoxide. Those solvent may be used alone or combination.

The bases suitable for use in this reaction are inorganic bases and organic bases. The inorganic bases include alkali metals, e.g. sodium hydroxide, potassium hydroxide, sodium carbonate, potassium carbonate, and organic bases include tertiary amines, e.g. triethylamine, and 4-dimethylaminopyridine, and 1,8-diazabicyclo[5,4,0]-7-undecene (DBU). The bases may be used in an equimolar or more.

The reaction temperature is in the range of 0° C. to the boiling point of the solvent used, preferably in the range of 0° to 150° C. The reaction period ranges from several minutes to 48 hours depending upon the amounts of reactants used, the reaction temperature, etc.

After completion of the reaction, the 3-(substituted phenyl)pyrazole derivatives of formula (I) can be obtained from the reaction product solution by an ordinary method, e.g. solvent extraction, and if necessary, by purification procedure such as recrystallization or column chromatography.

Salts of 3-(substituted phenyl)pyrazole derivatives of formula (I).

These salts are formed from acids including mineral acid, e.g. hydrochloric acid and sulfuric acid, and organic acids, e.g. p-toluenesulfonic acid. The production of these salts can be carried out by treating 3-(substituted phenyl)pyrazole derivatives of formula (I), obtained according to the above stated process, with the above-cited mineral acid or organic acid.

Typical examples of the 3-(substituted phenyl)pyrazole derivatives represented by formula (I) and the salts thereof are shown in Table 1.

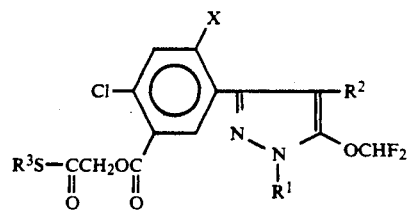

Formula (I)

TABLE 1

| | ($R^1$: $CH_3$, $R^2$: $C^1$) | | |
|---|---|---|---|
| Com'd No. | $R^3$ | X | Property |
| 1 | $C_2H_5$ | Cl | nD 1.5763 (20.7° C.) |
| 2 | i-$C_3H_7$ | Cl | nD 1.5684 (20.0° C.) |
| 3 | $CH_2CH=CH_2$ | Cl | nD 1.5818 (17.0° C.) |
| 4 | $CH_2-\bigcirc$ | Cl | nD 1.5938 (16.8° C.) |

Pyrazole derivaties of formula (II) that are starting materials for 3-(substituted phenyl)pyrazole derivatives of formula (I) or salts thereof can be produced, for instance, according to the following reaction schemes.

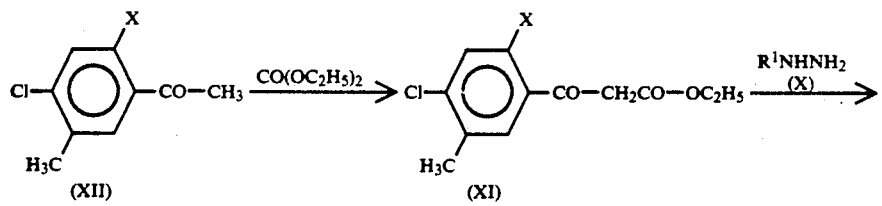

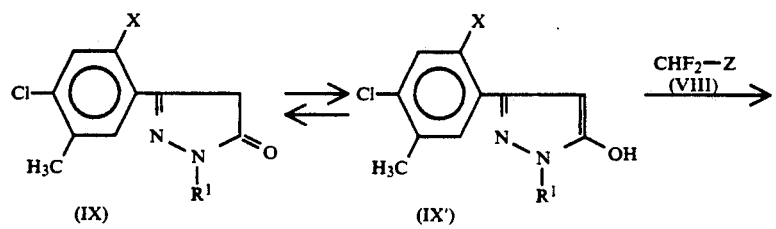

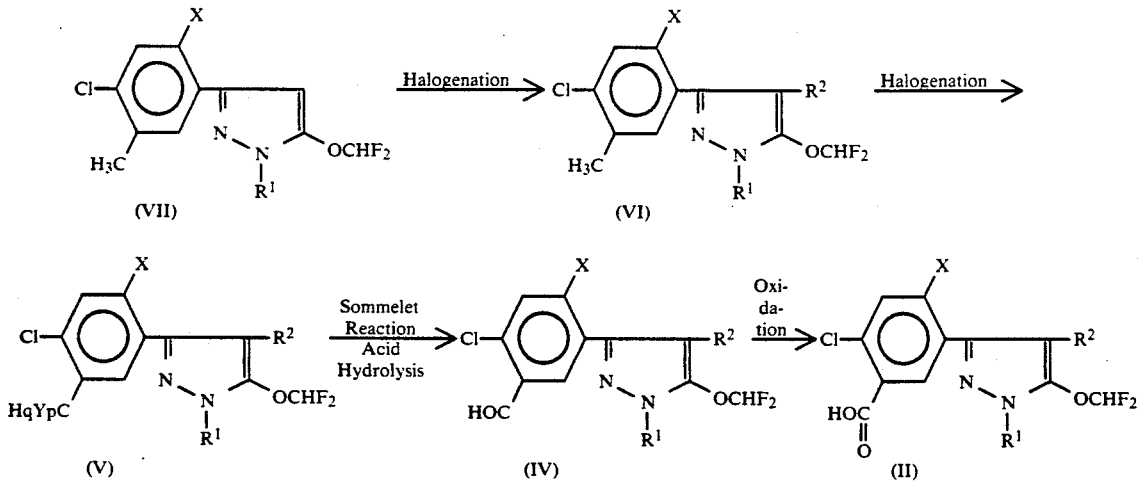

In the above equation, $R^1$, $R^2$, X and Z are as defined above, Y denotes halogen atom, and p and q denote each an integer of 1 or 2 with the provision that the sum of p and q is 3.

As shown above, a pyrazole derivative of formula (IX) can be prepared by reacting a compound of formula (XII) with diethyl carbonate, and reacting the resulting compound of formula (XI) with a hydrazine of formula (X).

The pyrazole derivative of formula (VI) can be produced from a pyrazole derivative of formula (IX); that is, the tautomer of pyrazole derivative of formula (IX') by reaction with a halide of formula (VIII), followed by halogenating the resulting pyrazole derivative of formula (VI).

The pyrazole derivative of formula (II) can be produced as follow; A pyrazole derivative of formula (VI) is reacted with a halogenating agent to give a pyrazole derivative of formula (V), which in turn is subjected to Sommelet reaction with hexamethylenetetramine and further hydrolyzed with an acid to give a pyrazole derivative of formula (IV), which in turn is oxidized to give a pyrazole derivative of formula (II).

The present invention is illustrated with a reference to typical examples thereof, which are not to restrict the scope of the invention.

EXAMPLE 1

Preparation of ethylthiocarbonylmethyl 5-(4-chloro-5-difluoromethoxy-1-methyl-1H-pyrazol-3-yl)-2,4-dichlorobenzoate (compound No. 1)

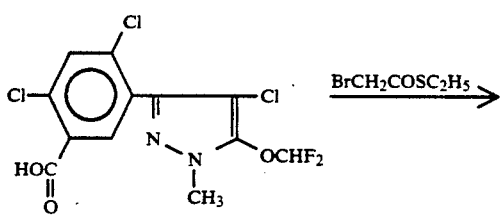

-continued

[structure showing product with C2H5SCCH2OC group]

A mixture of [5-(4-chloro-5-difluoromethoxy-1-methyl-1H-pyrazol-3-yl)]-2,4-dichlorobenzoic acid (0.32g, 0.8 mmole), S-ethyl bromothioacetate (0.34 g, 1.9 mmoles), 30 ml acetone and $K_2CO_3$ powder (0.26 g, 1.9 mmoles) was subjected to reaction under reflux for 4 hours. Then the reaction product solution, poured into ice-cold water, was extracted with ethyl acetate. The extract solution was washed with water, and dehydrated and concentrated. The residue was purified by column chromatography, giving the title compound (0.27 g), nD 1.5763 (20.7° C.), yield 66%.

The present inventive 3-(substituted phenyl)pyrazole derivatives represented by formula (I) and salts thereof are capable of controlling annual and perennial weeds grown in paddy fields, upland fields, orchards, and swamps, such as Barnyardgrass (*Echinochloa Crus-galli Beauv.*, an annual gramineous grass which is a typical weed strongly injurious, grown in paddy fields), Mizugayatsuri (*Cyperus serotinus Rottb.*, a perennial weed of Cyperaceae family, grown in swamps, ditches, and paddy fields), Urikawa (*Sagittaria pygmaea Mig.*, an injurious perennial weed of Alismataceae family, grown in swamps, diches, and paddy fields), Hotarui (*Scirpus juncoides Roxb.* subsp. juncoides, perennial cyperaceous weed grown in swamp water areas, and paddy fields), Wild oats (*Avena fatua L.*, an annual gramineous grass grown in plains, highlands, and upland fields), Large crabgrass (*Digitaraia adscendcus Henr.*, an annual gramineous grass which is a typical strongly injurious weed grown in upland fields and orchards), Curlydock (*Rumex japonicus Houtt.*, a perennial polygonaceous weed grown in upland fields and on roadsides), Umbrella sedge(*Cyperus Iria L.*, an annual cyperaceous weed grown in upland fields and on roadsides), Redroot pigweed (*Amaranthus vetroflexus L.*, an annual weed of Amaranthus family grown in upland fields, roadsides, and vacant lands), Cleavers (*Galium aparine L.*, a strongly injurious annual weed of Rubiaceae family grown in upland fields), Birdseye Speedwell (*Veronica persica L.*, a strongly injurious weed of Scrophulariaceae family grown in upland fields and orchards), Scented mayweed (*Matricaria chamomilla L.*, injurious composite weed grown in upland fields), Velvetleaf (*Abutilon theophrasti L.*, a strongly injurious weed of Malvaceae family grown in upland fields), Cocklebur (*Xanthium strumarium L.*, a strongly injurious annual composite weed grown in upland fields), and Tall morning glory (*Ipomoea purpurea Voigt*, a strongly injurious weed of Convolvulaceae family grown in upland fields).

Since the 3-(substituted phenyl)pyrazole derivatives of formula (I) and salts thereof exhibit excellent controlling effect on weeds before or immediately after germination, characteristic physiological activities of these compounds can be manifested by treating fields with the derivative or the salt before or after planting of useful plants therein (including fields where useful plants are already planted) in the stage prior to weed emergence or in the period from the initial stage of weed growth. However, the applications of the present inventive herbicides are not limited to such forms as stated above. The present herbicides can be applied to control not only weeds in paddy fields or upland fields but also general weeds grown in other places, for example, reaped fields, temporarily noncultivated paddy fields and upland fields, ridges between paddy fields, agricultural pathways, waterways, lands constructed for pasture, graveyards, parks, roads, playgrounds, unoccupied areas around buildings, reclaimed lands, railways, and forests. It is most desirable in economy as well to treat these areas with the present herbicides, before the end of the initial stage of weed growth, but the treatment is not limited to this but can be carried out in the middle stage of weed growth.

The 3-(substituted phenyl)pyrazole derivative of formula (I) or salt thereof, when applied as a herbicide, is generally made up, according to the customary procedure for preparing agricultural chemicals, into a form convenient for use. This is, the pyrazole derivative or salt thereof is blended with a suitable inert carrier and if necessary, further with an adjuvant, in proper ratios, and the mixture is made up into a suitable form of preparation, e.g. a suspension, emulsifiable concentrate, solution, wettable powder, granules, dusts, or tablets, through dissolution, dispersion, suspension, mixing, impregnation, adsorption, or sticking.

In the present invention, either solid or liquid inert carriers may be used.

Suitable materials as solid carriers include soybean flour, cereal flour, wood flour, bark flour, saw dust, powdered tobacco stalks, powdered walnut shells, bran, powdered cellulose, extraction residues of vegetables, powdered synthetic polymers or resins; clays(e.g. kaolin, bentonite, and acid clay), talcs (e.g. talc and pyrophyllite), silica powders or flakes (e.g. diatomaceous earth, silica sand, mica and white carbon, i.e. highly dispersed silicic acid, also called finely divided hydrated silica or hydrated silicic acid), activated carbon, powdered sulfur, powdered pumice, calcined diatomaceous earth, ground bricks, fly ash, sand, calcium carbonate powder, calcium phosphate powder, and other inorganic or mineral powders, chemical fertilizers (e.g. ammonium sulfate, ammonium nitrate, urea, and ammonium chloride) and compost. These materials may be used alone or in combination.

Suitable materials as liquid carriers include liquids which themselves show some solution-forming activity as well as liquids which do not show any solution-forming activity but can disperse active ingredients with the aid of adjuvants. Typical examples of such liquids, which may be used alone or in combination, are water, alcohols (including methanol, ethanol, isopropanol, butanol, and ethylene glycol), ketones (including acetone, methyl ethyl ketone, methyl isobutyl ketone, diisobutyl ketone, and cyclohexanone), ethers (including ethyl ether, dipropyl ether, dioxane, cellosolve, and tetrahydrofuran), aliphatic carbons (including gasoline, and mineral oils), aromatic hydrocarbons (including benzene, toluene, xylene, solvent naphtha, and alkyl naphthalenes), halogenated hydrocarbons (including dichloroethane, chloroform, and carbon tetrahydrochloride), esters (including ethyl acetate, diisopropyl phthalate, dibutylphthalate, and dioctyl phthalate), amides (including dimethylformamide, diethylformamide, and dimethylacetamide), nitriles (including acetonitrile), and dimethylsulfoxide.

The following materials are cited as typical examples of the adjuvants which may be used alone or in combination or may not be used at all.

For the purpose of emulsifying, dispersing, solubilizing, and/or wetting active ingredients, there may be used surface active agents such as polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninesulfonates, and higher alcohol sulfate esters.

For the purpose of stabilizing the dispersion of active ingredients, tackifying and/or binding them, there may be used adjuvants, for example, casein, cellulose, gum arabic, polyvinyl alcohol, turpentine oil, bran oil, bentonite, and ligninsulfonates.

For the purpose of improving flow properties of solid herbicidal products there may be used adjuvants, for example, wax, stearates, and alkylphosphates.

Adjuvants, e.g. naphthalene sulfonic acid condensation products, phosphoric acid condensation products, and polyphosphates, can be used as peptizers in dispersible herbicidal products.

Adjuvants, e.g. silicone oils, can also used as deforming agents.

The content of active ingredients may be varied as occasion demands; the suitable contents are from 0.01 to50% by weight for preparing, for example, dusts or granules as well as emulsifiable concentrates or wettable powders.

For the destroying various weeds or inhibiting their growth, the herbicidal composition containing the 3-(substituted phenyl)pyrazole derivatives of formula (I) or salt thereof as an active ingredient is apllied as such or after being properly diluted with or suspended in water or other media, in amounts effective for destroying weeds or inhibiting their growth, to the foliage and stalk of the weeds or to soil in the area where the emergence or growth of weeds is undesirable.

The amount of the present herbicidal composition to be used, depending upon various factors, e.g. the purpose of application, objective weeds, emergence or growth states of weeds and crops, emergence tendency of weeds, wheather, environmental conditions, form of the herbicidal composition, mode of the application, type or state of the application locus, and time of the application, is chosen properly according to the purpose from the range of 1.0 g to 10Kg, in terms of the amount of active ingredient, per hectare.

When the present herbicidal composition is applied to paddy fields or upland fields, it is desirable to choose such low doses as not to injure crops but to destroy weeds or control their growth. When the composition applied to non-farming areas, suitable doses of active ingredient for destroying the weeds are chosen from amounts of 100g/hectare and more.

The present herbicidal composition can be applied jointly with other herbicides for the purpose of expanding both the range of controllable weed species and the period of time when effective application are possible or for the purpose of reducing the dosage.

The following example illustrate herbicidal effects and formulations of the present inventive herbicidal composition without limiting the scope of the invention.

TEST EXAMPLE 1

Herbicidal Effect on Paddy Field Weeds of Post-Emergence Stage

Pots(1/10,000-are) were filled with soil to simulate a paddy field, then planted separately with seeds of barnyardgrass (BG) and hotarui (HI) and with tubers of mizugayatsuri (MG) and urikawa (UK), which are all injurious weeds grown in paddy fields, and were conditioned so that these weeds grew to 1-leaf stage.

Soil in each pot was sprayed with each of solutions containing compounds(listed in Table 1) of the present invention as active ingredients at a predetermined cocentration. 21 days later, the herbicidal effect was examined, the percentage of killed weeds were calculated in comparison with those on the untreated pot, and the herbicidal activity was judged and the chemical injury of a rice plant was examined at the same time and judged according to the following criterion:

| | Herbicidal activity |
| --- | --- |
| Rating | Percentage of killed weed |
| 5 | 95% or more |
| 4 | 70–95% (exclusive) |
| 3 | 50–70% (exclusive) |
| 2 | 30–50% (exclusive) |
| 1 | 10–30% (exclusive) |
| 0 | less than 10% |

| | Phytotoxicity |
| --- | --- |
| Rating | Degree of phytotoxicity |
| 0 | No phytotoxicity |
| 1 | Browning occurs but disappears in the initial growth stage, growth inhibition is not observed. |
| 2 | Browning and distinct growth inhibition are observed but normal conditions are soon restored. |
| 3 | Browning and growth inhibition are remarkable and restoration is slow. |
| 4 | Browning and growth inhibition are remarkable and some of the rice plants are killed. |
| 5 | All the crop plants are killed. |

For the comparison the following compounds were also tested.

Compound A: 3-phenyl-5-methylthiopyrazole, described on page 3 in Japanese Patent Application Kokai No. Sho. 52-91861; compound B: described in Example 1 on page 4 in the same patent application; compound C: compound No. 8 described in Japanese Patent Application Kokai No. Sho. 54-70270; compound D: compound No. 159 described on page 9 in Japanese Patent Application Kokai No. Sho. 55-9062.

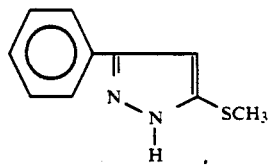

Compound A.

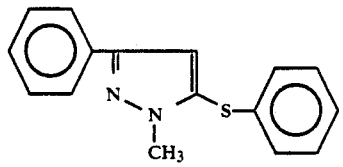

Compound B.

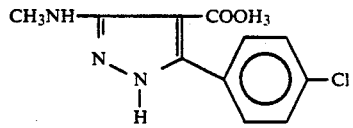

Compound C.

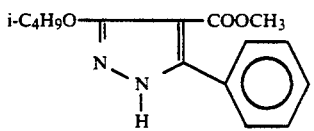

Compound D.

TABLE 2

| Comp'd No. | Amount of active ingredient Kg/ha | Phytotoxicity rice | Post-emergence treatment | | | |
| --- | --- | --- | --- | --- | --- | --- |
| | | | BG | HI | MG | UK |
| 1 | 5 | 5 | 5 | 5 | 5 | 5 |
| 2 | 5 | 5 | 5 | 5 | 5 | 5 |
| 3 | 5 | 5 | 5 | 5 | 5 | 5 |
| 4 | 5 | 5 | 5 | 5 | 5 | 5 |
| A | 5 | 0 | 0 | 0 | 0 | 0 |
| B | 5 | 0 | 2 | 0 | 0 | 0 |
| C | 5 | 0 | 0 | 0 | 0 | 0 |
| D | 5 | 0 | 0 | 0 | 0 | 0 |

As shown in Table 2, the present 3-(substituted phenyl)pyrazole derivatives or salt thereof, represented by the general formula (I), exhibit more excellent controlling effects on weeds than comparative compound A, B, C or D at post-emergence treatment in paddy fields. Even when the derivatives exhibit both herbicidal activity on weeds and phytotoxicity on crops at the same dosage, however, by the selection of a proper lower dosage, sufficient herbicidal activity is retained but phytotoxicity on crops reduced remarkably.

TEST EXAMPLE 2

Herbicidal Effect on Upland Field Weeds of Pre-Emergence Stage

Polyethylene vats of 10 cm W×20 cm L×5 cm depth were filled with soil, and sown respectively with seeds of barnyardgrass (BG), velvetleaf (VL), cocklebur (CB), birdseye speedwell (BS), cleavers (CV), which are upland field weeds, and sown respectively with seeds of soybean(SB) and wheat (WT) as upland field crops.

Soil in each pot was sprayed with each of solutions containing compounds(listed in Table 1) of the present invention as active ingredients at a predetermined concentration. 14 Days later, the herbicidal effect was examined, the percentage of killed weeds were calculated in the same manner as in Test Example 1, and the phytotoxicity of soybean and wheat plants were also examined and judged according to the criterion shown in the Test Example 1.

Results of the test are shown in Table 3.

TABLE 3

| Comp'd No. | Amount of active ingredient Kg/ha | Phyto-toxicity | | Pre-emergence treatment | | | | |
|---|---|---|---|---|---|---|---|---|
| | | WT | SB | BG | VL | CB | BS | CV |
| 1 | 0.8 | 0 | 2 | 4 | 5 | 5 | 5 | 5 |
| 2 | 0.8 | 2 | 3 | 4 | 4 | 3 | 5 | 5 |
| 3 | 0.2 | 0 | 0 | 2 | 2 | 0 | 5 | 0 |
| 4 | 0.2 | 0 | 0 | 2 | 0 | 0 | 5 | 0 |
| A | 5 | 0 | 0 | 0 | 0 | 0 | 0 | 0 |
| B | 5 | 0 | 0 | 0 | 0 | 0 | 0 | 0 |
| C | 5 | 0 | 0 | 0 | 0 | 0 | 0 | 0 |
| D | 5 | 0 | 0 | 0 | 0 | 0 | 0 | 0 |

As shown in Table 3, the present 3-(substituted phenyl)pyrazole derivatives or salt thereof, represented by the general formula (I), exhibit a greater, excellent controlling effect on weeds than comparative compound A, B, C or D at pre-emergence treatment in upland fields. Even when the derivatives exhibit both herbicidal activity on weeds and phytotoxicity on crops at the same dosage, however, by the selection of a proper lower dosage, sufficient herbicidal activity is retained but phytotoxicity on crops reduced remarkably.

TEST EXAMPLE 3

Herbicidal Effect on Upland Field Weeds of Post-Emergence Stage

Polyethylene vats of 10 cm W×20 cm L×5 cm depth were filled with soil, and sown with seeds of upland field weeds shown below and with seeds of soybean and wheat as upland field crops. These weeds and crops were grown to the leaf stages shown below. Then these weeds and crops were sprayed with solutions containing compounds (listed in Table 1) of the present invention as active ingredients at a predetermined concentration.

14 Days later, the herbicidal effect was examined, the percentages of killed weeds were calculated in the same manner as in Test Example 1, and the phytotoxicity of soybean and wheat plants was also examined and judged according to the criterion shown in the Test Example 1.

Species of test weeds and leaf stages thereof and leaf stages of test soybean and wheat plants.

| | |
|---|---|
| Barnyardgrass (BG) | 2-leaf stage |
| Velvetleaf (VL) | 2-leaf stage |
| Cocklebur (CB) | 1-leaf stage |
| Birdseye Speedwell (BS) | 1-leaf stage |
| Cleavers (CV) | 2-leaf stage |
| Wheat (WT) | 2-leaf stage |
| Soybean (SB) | 1-leaf stage |

Results of the test are shown in Table 4.

TABLE 4

| Comp'd No. | Amount of active ingredient Kg/ha | Phyto-toxicity | | Post-emergence treatment | | | | |
|---|---|---|---|---|---|---|---|---|
| | | WT | SB | BG | VL | CB | BS | CV |
| 1 | 0.8 | 2 | 5 | 5 | 5 | 5 | 5 | 5 |
| 2 | 0.8 | 2 | 5 | 4 | 5 | 5 | 5 | 5 |
| 3 | 0.2 | 2 | 5 | 4 | 5 | 5 | 5 | 5 |
| 4 | 0.2 | 2 | 5 | 4 | 5 | 5 | 5 | 5 |
| A | 5 | 0 | 2 | 0 | 3 | 1 | — | 3 |
| B | 5 | 0 | 1 | 0 | 2 | 0 | — | 2 |
| C | 5 | 0 | 1 | 0 | 1 | 0 | — | 1 |
| D | 5 | 0 | 2 | 2 | 3 | 1 | — | 3 |

As shown in Table 4, the present 3-(substituted phenyl)pyrazole derivatives or salt thereof, represented by the general formula (I), exhibit more excellent controlling effects on weeds than comparative compound A, B, C or D at post-emergence treatment in upland fields. Even when the invented derivatives exhibit both herbicidal activity on weeds and phytotoxicity on crops at the same dosage, by the selection of a proper lower dosage, sufficient herbicidal activity is retained and chemical injury on crops is diminished remarkably.

FORMULATION EXAMPLE 1

A wettable powder composition was prepared by uniform mixing and grinding of the following ingredients:

| | |
|---|---|
| Compound No. 1 | 50 parts |
| Clay-white carbon mixture | 45 parts |
| (Clay is the major component) | |
| Polyoxyethylene nonylphenyl ether | 5 parts |

FORMULATION EXAMPLE 2

A granular composition was prepared by uniform mixing and grinding of the following ingredients, kneading the mixture with a suitable amount of water, and granulating the kneaded mixture:

| | |
|---|---|
| Compound No. 4 | 5 parts |
| Bentonite-clay mixture | 90 parts |
| Calcium ligninsulfonate | 5 parts |

FORMULATION EXAMPLE 3

An emulsifiable concentrate was prepared by uniform mixing of the following ingredients:

| | |
|---|---|
| Compound No. 3. | 50 parts |
| Xylene | 40 parts |
| Mixture of polyoxyethylene nonylphenyl ether and calcium alkylbenzenesulfonate | 10 parts |

FORMULATION EXAMPLE 4

A wettable powder composition was prepared by uniform mixing and grinding of the following ingredients:

| | |
|---|---|
| Compound No. 2 | 50 parts |
| Clay-white carbon mixture | 45 parts |
| (Clay is the major component) | |

-continued

| | |
|---|---|
| Polyoxyethylene nonylphenyl ether | 5 parts |

What is claimed is:

1. A 3-(substituted phenyl)pyrazole derivative or a salt thereof, the derivative being represented by the general formula

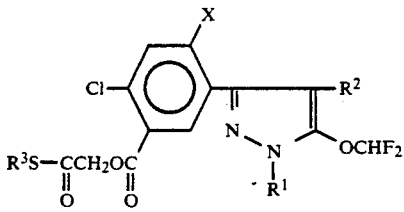
(I)

wherein,

X denotes halogen, R¹ denotes lower alkyl, R² denotes halogen and R³ denotes lower alkyl, lower alkenyl or benzyl group.

2. A 3-(substituted phenyl)pyrazole derivative or a salt thereof according to claim 1, wherein X denotes chlorine; R¹ denotes methyl; R² denotes chlorine; and R³ denotes lower alkyl.

3. A 3-(substituted phenyl)pyrazole derivative or a salt thereof according to claim 2, which is ethylthiocarbonylmethyl 5-(4-chloro-5-difluoromethoxy-1-methyl-1H-pyrazol-3-yl)-2,4-dichlorobenzoate, or i-propylthiocarbonylmethyl 5-(4-chloro-5-difluoromethoxy-1-methyl-1H-pyrazol-3-yl)-2,4-dichlorobenzoate.

4. A herbicidal composition which contains a 3-(substituted phenyl)pyrazole derivative or a salt thereof as an active ingredient, the pyrazole derivative being represented by the general formula

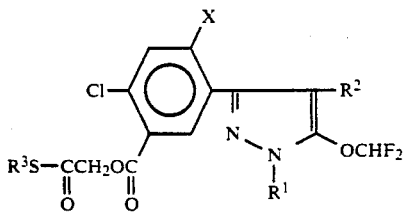
(I)

wherein,

X denotes halogen, R¹ denotes lower alkyl, R² denotes halogen and R³ denotes lower alkyl, lower alkenyl or benzyl group.

5. A herbicidal composition according to claim 4, wherein:

X denotes chlorine; R¹ denotes methyl; R² denotes chlorine; and R³ denotes lower alkyl.

6. A herbicidal composition according to claim 5, wherein the pyrazole derivative is ethylthiocarbonylmethyl 5-(4-chloro-5-difluoromethoxy-1-methyl-1H-pyrazol-3-yl)-2,4-dichlorobenzoate, or i-propylthiocarbonylmethyl 5-(4-chloro-5-diflruoromethoxy-1-methyl-1H-pyrazol-3-yl)-2,4-dichlorobenzoate.

7. A method for controlling undesirable plants which comprises applying a herbicidal composition containing a 3-(substituted phenyl)pyrazole derivative represented by the following general formula (I) or a salt of the derivative as a active ingredient, in a dose of 1.0 g to 10 Kg in terms of the quantity of active ingredient per hectare,

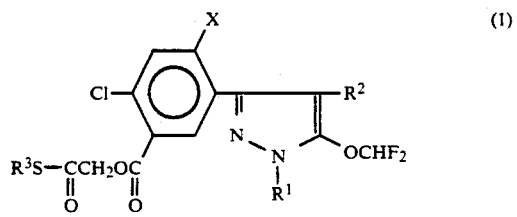
(I)

wherein,

X denotes halogen, R¹ denotes lower alkyl, R² denotes halogen and R³ denotes lower alkyl, lower alkenyl, or benzyl, group.

8. The method of claim 7, wherein upland fields are treated with said herbicidal composition.

* * * * *